United States Patent
Rosenthal et al.

(10) Patent No.: US 8,499,821 B2
(45) Date of Patent: Aug. 6, 2013

(54) METHOD FOR DETECTING AND CLASSIFYING SURFACE DEFECTS ON CONTINUOUSLY CAST SLABS

(75) Inventors: Dieter Rosenthal, Niederfischbach (DE); Stephan Schulze, Ratingen (DE); Ingo Schuster, Willich (DE); Peter Sudau, Hilchenbach (DE); Rainer Fackert, Meinborn (DE); Andreas Weinert, Essen (DE); Wilfried Schumacher, Heiligenhaus (DE)

(73) Assignee: SMS Siemag AG, Düsseldorf (DE)

( * ) Notice: Subject to any disclaimer, the term of this patent is extended or adjusted under 35 U.S.C. 154(b) by 340 days.

(21) Appl. No.: 12/597,360

(22) PCT Filed: Apr. 2, 2008

(86) PCT No.: PCT/DE2008/000582
§ 371 (c)(1),
(2), (4) Date: Jan. 21, 2010

(87) PCT Pub. No.: WO2008/128504
PCT Pub. Date: Oct. 30, 2008

(65) Prior Publication Data
US 2010/0132910 A1 Jun. 3, 2010

(30) Foreign Application Priority Data
Apr. 24, 2007 (DE) .......... 10 2007 020 240

(51) Int. Cl.
*B22D 11/16* (2006.01)
(52) U.S. Cl.
USPC .............. 164/452; 164/451; 382/141
(58) Field of Classification Search
USPC ................. 164/451, 452; 382/141
See application file for complete search history.

(56) References Cited

U.S. PATENT DOCUMENTS

| 4,338,822 | A * | 7/1982 | Yamaguchi et al. ........... 73/643 |
| 4,519,041 | A | 5/1985 | Fant et al. |
| 4,620,353 | A * | 11/1986 | Pryor ............................. 164/4.1 |
| 6,184,924 | B1 | 2/2001 | Schneider et al. |
| 6,436,205 | B1 | 8/2002 | Behrens et al. |
| 6,842,656 | B1 | 1/2005 | Burkhardt et al. |

FOREIGN PATENT DOCUMENTS

| DE | 19930173 | 1/2001 |
| EP | 0093422 | 11/1983 |
| EP | 0880023 | 11/1998 |
| EP | 1097764 | 5/2001 |

* cited by examiner

*Primary Examiner* — Nicholas P D'Aniello
(74) *Attorney, Agent, or Firm* — Cozen O'Connor

(57) ABSTRACT

A method for the detection and classification of surface defects on continuously cast products using topographical information about the appearance of continuously cast surface defects and/or flaws are determined with respect to their exact position, evaluated with respect to their location and dimensions, and eliminated in accordance with the evaluation prior to further machining of the product, or are prevented by optimizing the process. The defects and/or flaws on the slab surface of the continuously cast preliminary product are detected and are stored with respect to their exact position and a detection of defects and/or flaws on the finished product is carried out and stored with respect to their exact position, and in that the information from the preliminary product is then compared with the information from the surface inspection on the finished product. Only the information which has led to, or can lead to, defects on the finished product is considered for the elimination of defects and/or flaws on the preliminary product.

16 Claims, 2 Drawing Sheets

Slab surface monitoring system    Strip surface monitoring system

METHOD FOR DETECTING AND CLASSIFYING SURFACE DEFECTS ON CONTINUOUSLY CAST SLABS

PRIORITY CLAIM

This is a U.S. national stage of application No. PCT/DE2008/000582, filed on Apr. 2, 2008, which claims Priority to the German Application No.: 10 2007 020 240.9, filed: Apr. 24, 2007; the contents of both being incorporated herein by reference.

BACKGROUND OF THE INVENTION

1. Field of the Invention

The invention is directed to a method for detecting and classifying surface defects on continuously cast products using topographical information relating to the appearance of continuously cast surfaces in which defects and/or flaws are determined and evaluated with respect to their exact position.

2. Prior Art

Numerous methods are known for detecting and eliminating surface defects on materials such as continuously cast products. For example, according to EP 0 880 023 A1, surface defects are detected automatically and are subsequently removed by a grinding machine before further processing, that is, before finish rolling in a roll mill. The grinding machine operates reversibly so that successive defects or defects which are scattered over large surface areas are determined by an inspection device arranged in front of and behind the grinding machine and can then be eliminated.

The defects are evaluated based on a comparison with stored models so that the quality of defect detection and, therefore, elimination depends upon the stored material. Accordingly, superfluous work steps cannot always be avoided.

SUMMARY OF THE INVENTION

In principle, only those surface defects which lead to defects in the rolled product, e.g., hot strip or sheet, should be detected and evaluated. It is not necessary to eliminate all of the other flaws on the slab surface.

It is an object of the invention to provide a method by which a more reliable evaluation and subsequent elimination of defects is achieved.

The information obtained is used in the assessment to eliminate defects before further machining of the product or for timely determination and classification of the possible quality of the finished product.

A method for the detection and classification of surface defects on continuously cast products using topographical information about the appearance of continuously cast surfaces comprises determining defects and/or flaws with respect to their exact position, evaluating the defects/flaws with respect to their location and dimensions, and eliminating the defects/flaws in accordance with the evaluation prior to further machining of the product. The above-stated object is met in that the defects and/or flaws on the slab surface of the continuously cast preliminary product are detected and stored with respect to their exact position and a detection of defects and/or flaws on the finished product is carried out and stored with respect to their exact position the information from the preliminary product is then compared with the information from the surface inspection on the finished product, and only the information which has led to, or can lead to, defects on the finished product is taken into account for the elimination of defects and/or flaws on the preliminary product.

According to one embodiment of the invention, surface topography of the continuously cast slabs is determined by suitable methods. Such methods are optical methods operating in the visible or invisible spectrum of light or microwave-based methods. In the visible range, fringe projection methods and stereoscopic methods are used. Laser-based methods are also possible. The information about surface topography acquired by means of one or more of these methods is stored in a location-dependent manner, i.e., corresponding to position. The evaluation of detected changes in topography can be carried out by suitable classifying methods, e.g., neural networks, or the like.

According to one embodiment of the invention, method is characterized by a learning phase during which the classification methods are optimized so as to distinguish between irrelevant surface flaws and relevant surface defects which lead to, or have led to, surface defects on the finish-rolled products, in this case, hot strip or sheet.

The results of a surface inspection on the finished produced are preferably linked to the slab inspection system. In particular, the absolute position of the defects on the finished product is converted to the absolute position on the slab surface. Pass sequence data, such as total degree of deformation and ratio of cross rolling to longitudinal rolling, are incorporated in the model. The information on the position of a likely surface defect on the slab is stored and compared with the information determined by the inspection system following finish rolling so that self-learning occurs.

Relationships found by classifying methods, e.g., neural networks, between the topography and the probability of the occurrence of surface defects are used for a prediction.

The method is able to measure both hot and cold slab surfaces, and either the slab or the measuring device is moved during measurement. The movement is carried out in discrete increments or continuously.

The topographical information obtained is stored with its absolute position in accordance with the results of the classification.

As was mentioned above, the decision about whether or not a surface defect exists which can be removed prior to further processing of the slab surface or which leads to a loss of quality on the finished product makes a learning phase necessary. This learning is carried out manually through inspector guidelines, but is then subject to subjective errors. Therefore, according to one embodiment of the invention, this problem is solved by preferably linking to surface inspection systems on the finished product.

When the method is used in an unlinked installation (slab continuous casting plant and rolling mill) without direct use of the slab or with externally purchased slabs, this learning algorithm is implemented using a long-term database.

Another embodiment consists in the use of this system within a framework of an automated slab inspection. In this case defects are marked by a marking robot to facilitate location for repair purposes. Position information is also forwarded to a machining center for automatic repairs.

DETAILED DESCRIPTION OF THE DRAWINGS

Figure 1:
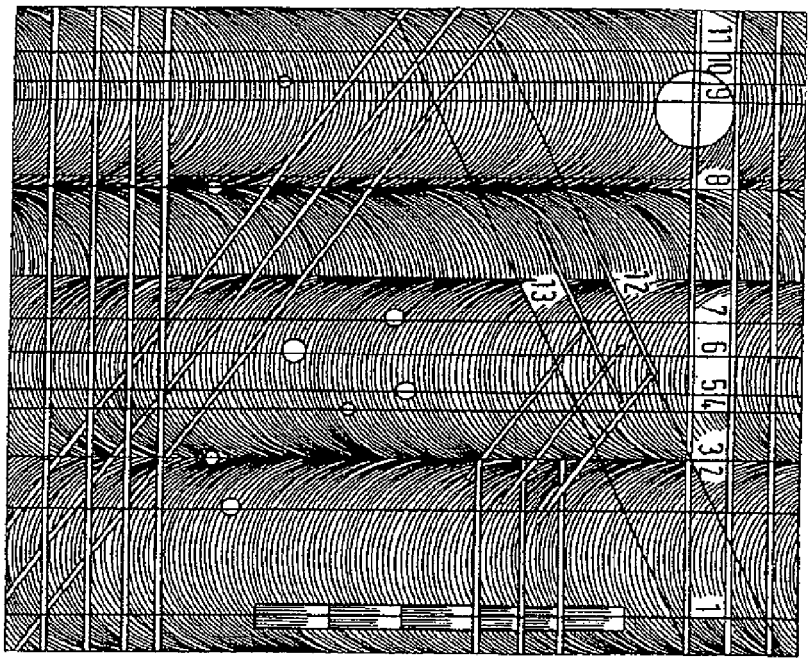
FIG. 1 is a sample in which artificial flaws, i.e., defects, have been incorporated.

Flaws along lines 1-13 were artificially created in a sample for illustrating the method as shown in FIG. 1. The lines labeled are shown on the right-hand side of FIG. 1. Line 5 is referred to by way of example for the following description.

Figure 2:
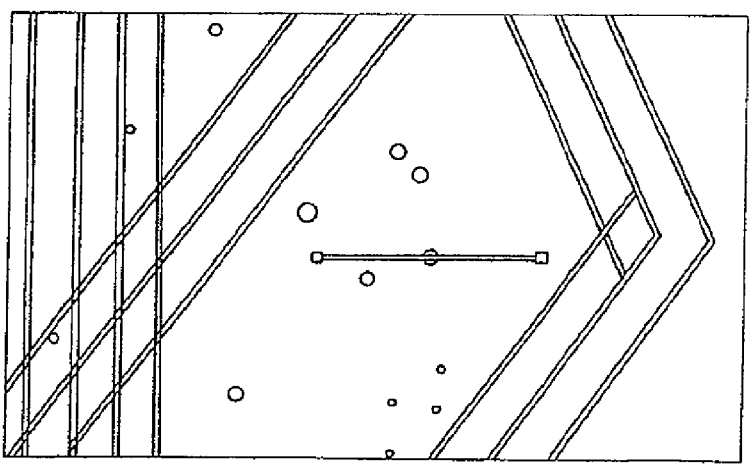
FIG. 2 is a result of a measurement of the sample by a fringe projection method, specifically line 5 in FIG. 1.
Figure 3:
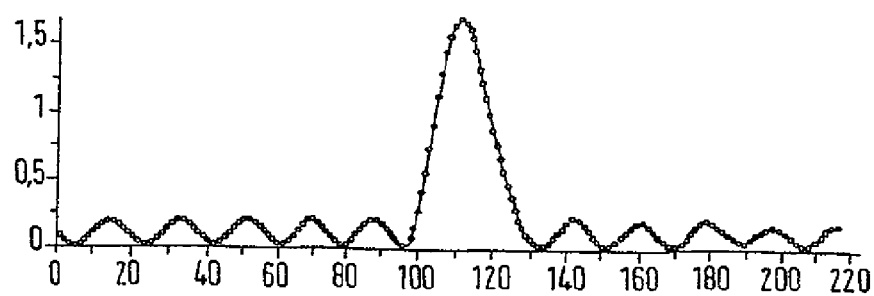
FIG. 3 is a topographical evaluation of the lines in FIG. 1.

The sample, including the flaws along lines 1-13, was measured using a fringe projection method. The results for line 5 are shown in FIG. 2. The topographical information is correlated with a punctiform defect as shown in FIG. 3.

Figure 4:
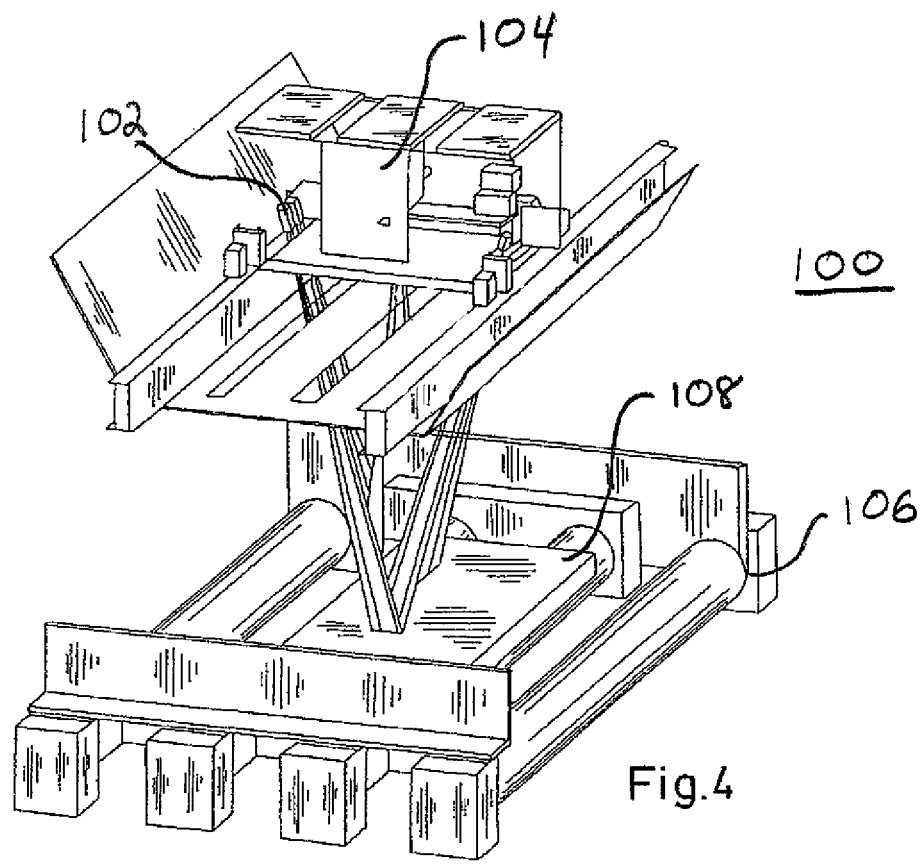
FIG. 4 is a measuring device.

FIG. 4 shows an example for the arrangement 100 of the measuring device with projector 102 and camera 104 above a table roller 106 serving to transport the slab 108.

Figure 5:
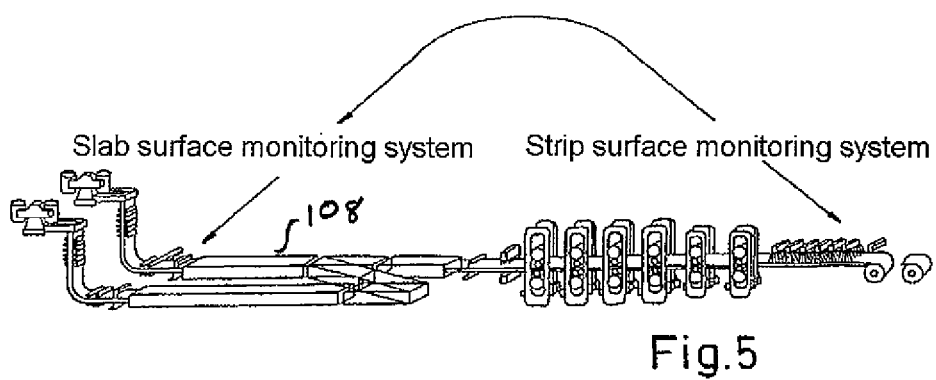
FIG. 5 is the principle of the inspecting and evaluating system according to one embodiment of the invention.

FIG. 5 shows the basic concept, wherein the defects and/or flaws on the preliminary product, i.e., the slab 108, are detected by the first surface inspection, and a second inspection device then detects defects and/or flaws on the rolled finished product. Based on the comparison that is then carried out, conclusions are reached concerning which of the defects initially detected result in a defect on the finished product so that a learning process is initiated which leads to an improved evaluation of defects on the preliminary product with the result that only those defects which are disadvantageous for the finished product need be eliminated.

Thus, while there have shown and described and pointed out fundamental novel features of the invention as applied to a preferred embodiment thereof, it will be understood that various omissions and substitutions and changes in the form and details of the devices illustrated, and in their operation, may be made by those skilled in the art without departing from the spirit of the invention. For example, it is expressly intended that all combinations of those elements and/or method steps which perform substantially the same function in substantially the same way to achieve the same results are within the scope of the invention. Moreover, it should be recognized that structures and/or elements and/or method steps shown and/or described in connection with any disclosed form or embodiment of the invention may be incorporated in any other disclosed or described or suggested form or embodiment as a general matter of design choice. It is the intention, therefore, to be limited only as indicated by the scope of the claims appended hereto.

The invention claimed is:

1. A method for the detection and elimination of surface defects on continuously cast products, the method comprising:
   a.) detecting continuously cast defects and dimension of each of the detected continuously cast defects on a surface of a continuously cast product and evaluating a position and dimension of each of the detected continuously cast defects;
   b.) storing continuously cast defect information including the position and dimension for the each of the continuously cast defects;
   c.) processing the continuously cast product to create a finished product;
   d.) detecting finished product defects on the finished product;
   e.) storing the finished product defect information with respect to the exact position of the finished product defect on the finished product;
   f.) comparing the detected finished product defects with the detected continuously cast product defects to determine information that can lead to the finished product defects; and
   g.) based at least in part on the information determined by the comparing, eliminating or preventing the finished product defects on subsequently produced finished products,
   wherein a relationship between the finished product defects on the finished product and the continuously cast defects on the continuously cast product and a probability of occurrence of surface defects are used for a defect prediction,
   wherein the method is a learning process and based on the defect prediction, only continuously cast defects that would result in finished product defects are eliminated on the subsequently produced continuously cast products.

2. The method according to claim 1, wherein the continuously cast defect information and the finished product defect information comprises topographical information determined by an optical method operating in at least one of a visible or invisible region.

3. The method according to claim 1, wherein the continuously cast defect information and the finished product defect information comprises topographical information determined by at least one of a laser-based method and a microwave-based method.

4. The method according to claim 2, wherein the continuously cast defect information and the finished product defect information topographical information is obtained by at least one of a projection method and a stereoscopic method.

5. The method according to claim 1, wherein the continuously cast defect information and the finished product defect information comprises topographical information determined by at least one of visible and invisible sources of electromagnetic radiation.

6. The method according to claim 1, wherein the defects are stored in a location-dependent manner and evaluated by a classifying method.

7. The method according to claim 1, wherein steps a.-f. are performed in a learning phase wherein only defects on the continuously cast product surface which lead to surface defects on a finish-rolled product are assessed as defective, wherein the finished—rolled product comprises at least one of a hot strip or sheet.

8. The method according claim 1, wherein the step of comparing comprises converting an absolute position of the finished product defects on the finished product to an absolute position on the continuously cast product, wherein pass sequence data is incorporated in the converting.

9. The method according to claim 8, wherein topographical information of the finished product defects and continuously cast defects are stored with the absolute positions depending upon the results of the comparing.

10. The method according to claim 1, wherein at least one of the finished product defects on the finished product and the continuously cast defects on the continuously cast product are marked by a marking robot.

11. The method according to claim 1, wherein information obtained from the comparing is forwarded to a machining center for automatic repair of the continuously cast product.

12. The method according to claim 6, wherein the classifying method utilizes a neural network.

13. The method according claim 8, wherein pass sequence data including at least one of a total degree of deformation and a ratio of transverse rolling to longitudinal rolling is used in the step of converting.

14. The method according to claim 1, wherein a respective detected continuously cast defect is treated only after it has been detected at two different steps.

15. The method according to claim 10, wherein the marking is performed prior to rolling the continuously cast products.

16. The method according to claim 14, wherein a respective detected continuously cast defect is treated only after the second detection of the defect on a specific slab.

* * * * *